(12) United States Patent
Nagahama et al.

(10) Patent No.: US 11,136,287 B2
(45) Date of Patent: Oct. 5, 2021

(54) METHOD FOR PRODUCING N-BENZYL-2-BROMO-3-METHOXYPROPIONAMIDE AND INTERMEDIATES THEREOF

(71) Applicant: API CORPORATION, Tokyo (JP)

(72) Inventors: Masaki Nagahama, Fukuoka (JP); Kenta Saito, Fukuoka (JP)

(73) Assignee: API CORPORATION, Tokyo (JP)

(*) Notice: Subject to any disclaimer, the term of this patent is extended or adjusted under 35 U.S.C. 154(b) by 415 days.

(21) Appl. No.: 16/078,889

(22) PCT Filed: Nov. 21, 2017

(86) PCT No.: PCT/JP2017/041899
§ 371 (c)(1),
(2) Date: Aug. 22, 2018

(87) PCT Pub. No.: WO2018/159028
PCT Pub. Date: Sep. 7, 2018

(65) Prior Publication Data
US 2020/0115322 A1  Apr. 16, 2020

(30) Foreign Application Priority Data
Mar. 1, 2017 (JP) .............................. JP2017-038574

(51) Int. Cl.
C07C 231/02 (2006.01)
C07C 231/12 (2006.01)
C07C 235/06 (2006.01)

(52) U.S. Cl.
CPC .......... *C07C 231/02* (2013.01); *C07C 231/12* (2013.01); *C07C 235/06* (2013.01)

(58) Field of Classification Search
None
See application file for complete search history.

(56) References Cited

U.S. PATENT DOCUMENTS

| | | | | |
|---|---|---|---|---|
| 4,206,143 | A * | 6/1980 | Wenzel | C07C 231/02 564/135 |
| 9,512,062 | B2 * | 12/2016 | Knebel | C07C 231/02 |
| 2011/0218312 | A1 * | 9/2011 | Knebel | C08F 220/56 526/303.1 |
| 2011/0263899 | A1 | 10/2011 | Bouvy et al. | |
| 2012/0209022 | A1 * | 8/2012 | Pandey | C07C 271/22 560/24 |
| 2013/0123537 | A1 * | 5/2013 | Garimella | C07C 231/24 564/158 |
| 2013/0317109 | A1 * | 11/2013 | Kvarnstrom Branneby | C07C 231/12 514/616 |
| 2014/0018577 | A1 * | 1/2014 | Merschaert | C07C 227/34 564/136 |
| 2014/0288330 | A1 | 9/2014 | Broell et al. | |
| 2014/0323738 | A1 * | 10/2014 | Davuluri | C07C 231/02 548/215 |
| 2015/0025274 | A1 * | 1/2015 | Bernal-Vazquez | C07C 231/02 564/139 |
| 2016/0004682 | A1 | 2/2016 | Ito et al. | |
| 2016/0046828 | A1 | 2/2016 | Ito et al. | |
| 2016/0060210 | A1 * | 3/2016 | Ravi | C07C 231/12 564/191 |
| 2016/0332958 | A1 * | 11/2016 | Lim | C07C 231/02 |
| 2017/0266353 | A1 | 9/2017 | Murphy et al. | |
| 2018/0371013 | A1 * | 12/2018 | Nagahama | A61P 25/04 |
| 2019/0047944 | A1 * | 2/2019 | Sathe | C07C 231/02 |
| 2021/0078940 | A1 * | 3/2021 | Nagahama | C07C 51/305 |

FOREIGN PATENT DOCUMENTS

| | | | | |
|---|---|---|---|---|
| CN | 102070747 | A | 5/2011 | |
| JP | 2002-363129 | A | 12/2002 | |
| JP | 2002363129 | A * | 12/2002 | |
| JP | 2012-512217 | A | 5/2012 | |
| JP | 2015-502375 | A | 1/2015 | |
| WO | 2010/052011 | A1 | 5/2010 | |
| WO | 2012/069855 | A1 | 5/2012 | |
| WO | 2013/072933 | | 5/2013 | |
| WO | WO-2013072933 | A2 * | 5/2013 | ........... C07C 237/06 |
| WO | 2014/133135 | A1 | 9/2014 | |
| WO | 2015/175665 | | 11/2015 | |

OTHER PUBLICATIONS

English-Language Machine Translation of JP 2002363129 (2002) (Year: 2002).*
CAS Abstract of H. Oshiki et al, JP 2002363129 (2002) (Year: 2002).*
N.G. Anderson, Practical Process & Research Development, 81-111 (2000) (Year: 2000).*
CAS Abstractor Benzylamine and Predicted Properties (1984) (Year: 1984).*
Examination Report, India Patent Office, Application No. 201917037980, dated Feb. 21, 2020.
Bradley J. Sparks et al., "Mussel-Inspired Thiol-Ene Polymer Networks: Influencing Network Properties and Adhesion with Catechol Functionality", Chemistry of Materials, American Chemical Society, vol. 24, No. 18, 2012, pp. 3633-3642.

(Continued)

Primary Examiner — Alexander R Pagano
(74) Attorney, Agent, or Firm — Greenblum & Bernstein, P.L.C.

(57) ABSTRACT

The present invention provides an industrially-preferable method for safely producing N-benzyl-2-bromo-3-methoxypropionamide at a high yield but at low cost. The method for producing of the present invention includes: in sequence, an amidation process that causes diacrylic anhydride to react with benzylamine in a solvent to obtain N-benzylacrylamide; a bromination process that causes N-benzylacrylamide to react with bromine in a solvent to obtain N-benzyl-2,3-dibromopropionamide; and a methoxylation process that causes N-benzyl-2,3-dibromopropionamide to react with methanol in the presence of a base to obtain N-benzyl-2-bromo-3-methoxypropionamide.

10 Claims, No Drawings

(56) References Cited

OTHER PUBLICATIONS

Yong-Seok Choi et al., "Mussel-Inspired Dopamine- and Plant-Based Cardanol-Containing Polymer Coatings for Multifunctional Filtration Membranes", ACS Applied Materials & Interfaces, American Chemical Society, vol. 6, No. 23, 2014, pp. 21297-21307.
International Search Report issued with respect to Patent Application No. PCT/JP2017/041899, dated Feb. 27, 2018.
Sachin Wadavrao et al., "A Non-infringing Route for Enantioselective Synthesis of Antiepileptic Agent Lacosamide", received Jul. 29, 2013, 3383-3386.
Gottfried Blaschke et al., "Untersuchung chromatographischer Racemattrennungen, VI", 1976, S1967-2344.
Nils Retzmann et al., "Host-guest-driven color change in water: influence of cyclodextrin on the structure of a copper complex of poly((4-hydroxy-3-(pyridine-3-yldiazenyl)phenethyl)methacrylamide-co-dimethylacrylamide)", received Apr. 2, 2014, 2480-2483.
European Search Report, European Patent Office, Application No. 17894658.8, dated Jan. 17, 2020.
European Office Action issued with respect to European application No. 17 894 658.8, dated Nov. 17, 2020.

* cited by examiner

METHOD FOR PRODUCING N-BENZYL-2-BROMO-3-METHOXYPROPIONAMIDE AND INTERMEDIATES THEREOF

FIELD

The present invention relates to a method for generating N-benzyl-2-bromo-3-methoxypropionamide and intermediates thereof.

BACKGROUND

N-benzyl-2-bromo-3-methoxypropionamide (hereinafter, sometimes abbreviated to "BMBA") is used as an intermediate for synthesizing lacosamide, which is a medicine efficacious for treatment for epilepsy, and various methods for generating N-benzyl-2-bromo-3-methoxypropionamide have been known.

In Patent Literature 1, 2-Bromo-3-methoxypropionic acid, which is one of the intermediates, is synthesized using 2,3-dibromopropionic acid alkyl or a derivative thereof as a starting material. Furthermore, the Literature also discloses a method for obtaining BMBA by synthesizing a mixed acid anhydrate from 2-bromo-3-methoxypropione acid using alkyl chloroformate and then causing the synthesized mixed acid anhydrate to react with benzyl amine.

However, since the method described in Patent Literature 1 uses expensive 2,3-dibromopropionic acid alkyl or a derivative thereof and alkyl chloroformate, an more inexpensive method has been demanded from an industrial viewpoint. Furthermore, the intermediate 2-bromo-3-methoxypropionic acid, which has a high solubility to water, requires for undergoing concentration of the reacting solution and multiple-time extraction from the aqueous phase using isobutyl acetate under an over acidity condition in order to increase the recovery ratio thereof. Consequently, the method is not a satisfactory industrial method for generating from the aspect of generation efficiency.

In Patent Literature 2, acrylonitrile is derived into acrylamide under the presence of sulfuric acid, and acrylamide is caused to react with benzyl alcohol to synthesize intermediate N-benzylacrylamide. Patent Literature 2 also discloses a method for generating that derives N-benzylacrylamide into BMBA.

However, the method of Patent Literature 2 needs to use acrylonitrile as a material and a solvent, and therefore in cases where the method is to be executed in an industrial batch reaction process, the residence times of acrylonitrile and acrylamide to be generated are prolonged and unintended polymerization easily occurs and accompanies reaction heat, which is hardly controlled. Furthermore, when excessive acrylonitrile is to be removed through evaporation through vacuum condensation, the polymerization is enhanced under an anoxia state or under a heated condition, and consequently there is a possibility that the polymerization product having a high viscosity blocks the capacitor. For the above, a safer method for generating is demanded from the industrial viewpoint. The yields of N-benzyl-2,3-dibromopropionamide and BMBA both to benzyl alcohol are calculated to be as low as 64% and 62%, respectively, from the result of Example 1 of Patent Literature 2. In addition to above, the method of Patent Literature 2 uses a large amount of concentrated sulfuric acid, which requires a reaction container made of high-quality material and a treatment of a large amount of waste solution of over acidity. A method for generating, which is lower impact on environment, has been demanded.

PRIOR ART REFERENCE

[Patent Literature 1] WO2010/052011
[Patent Literature 2] WO2012/069855

SUMMARY OF INVENTION

Problems to be Solved by Invention

With the foregoing problems in view, the object of the present invention is to provide an industrially-superior synthesizing route that can safely generate N-benzyl-2-bromo-3-methoxypropionamide at a high yield and a low cost.

Means to Solve the Problems

As a result of enthusiastic development, Inventors have found that N-benzyl-2-bromo-3-methoxypropionamide can be safely generated at a high yield and a low cost through a process of causing diacrylic anhydride to react with benzylamine to obtain N-benzylacrylamide and completed the present invention.

In other words, the present invention provides the following embodiments.

[1] A method for producing N-benzyl-2-bromo-3-methoxypropionamide including: in sequence, an amidation process that causes diacrylic anhydride to react with benzylamine in a solvent to obtain N-benzylacrylamide; a bromination process that causes N-benzylacrylamide to react with bromine in a solvent to obtain N-benzyl-2,3-dibromopropionamide; and a methoxylation process that causes N-benzyl-2,3-dibromopropionamide to react with methanol in the presence of a base to obtain N-benzyl-2-bromo-3-methoxypropionamide.

[2] The method according to [1], wherein diacrylic anhydride used in the amidation process is obtained by causing acrylic acid to react with a condensation agent in a solvent.

[3] The method according to [1] or [2], wherein the solvent used in the amidation process is a mixture solvent of an organic solvent and water.

[4] The method according to one of [1]-[3], wherein the solvent used in the amidation process contains a base.

[5] A method for producing N-benzyl-2,3-dibromopropionamide including: in sequence, an amidation process that causes diacrylic anhydride to react with benzylamine in a solvent to obtain N-benzylacrylamide; and a bromination process that causes N-benzylacrylamide to react with bromine in a solvent to obtain N-benzyl-2,3-dibromopropionamide.

[6] The method according to [5], wherein diacrylic anhydride used in the amidation process is obtained by causing acrylic acid to react with a condensation agent in a solvent.

[7] The method according to [6], wherein the condensation agent is a carbodiimide-based condensation agent.

[8] The method according to one of [5]-[7], wherein the solvent used in the amidation process is a mixture solvent of an organic solvent and water.

[9] The method according to one of [5]-[8], wherein the solvent used in the amidation process contains a base.

[10] A method for producing N-benzylacrylamide including an amidation process that causes diacrylic anhydride to react with benzylamine in a solvent to obtain N-benzylacrylamide.

[11] The method according to [10], wherein diacrylic anhydride used in the amidation process is obtained by causing acrylic acid to react with a condensation agent in a solvent.

[12] The method according to [11], wherein the condensation agent is a carbodiimide-based condensation agent.

[13] The method according to one of [10]-[12], wherein the solvent used in the amidation process is a mixture solvent of an organic solvent and water.

[14] The method according to one of [10]-[13], wherein the solvent used in the amidation process contains a base.

[15] The method according to one of [10]-[14], wherein the solvent used in the amidation process is a mixture solvent of a hydrophobic organic solvent and water, and contains a base in a aqueous phase.

Effects of Invention

The present invention can safely produce N-benzyl-2-bromo-3-methoxypropionamide at a high yield and a low cost, and consequently brings industrial advantages. Furthermore, the present invention can also provide a method for safely producing intermediates efficacious in producing N-benzyl-2-bromo-3-methoxypropionamide at a high yield and a low cost.

EMBODIMENT TO CARRY OUT INVENTION

Hereinafter, description will now be made in relation to the method for producing of the present invention. The following embodiment is merely example of an embodiment of the present invention, but the present invention is not limited to the embodiment. The present invention can be arbitrarily modified without departing from the scope of the invention. In this description, the notation of a numeral range of, for example, "1 to 100" includes both the lower limit "1" and the upper limit "100". The same is applied to other numeric ranges.

1. Method for Producing N-benzyl2-bromo-3-methoxypropionamide

The method for producing BMBA of the present invention is represented by the following synthesizing scheme. Namely, the scheme includes at least three steps of, in sequence, an amidation process that obtains N-benzylacrylamide (hereinafter, sometimes referred to as "NBA") represented by Formula (3) from diacrylic anhydride represented by Formula (2) and benzylamine; a bromination process that obtains N-benzyl-2,3-dibromopropionamide (hereinafter, sometimes referred to as "BBA") represented by Formula (4) from NBA and bromine; and a methoxylation process that obtains N-benzyl-2-bromo-3-methoxypropionamide (hereinafter, sometimes referred to as "BMBA") represented by Formula (5) from BBA, methanol, and a base. The method for producing BMBA of the present invention may further include, before the amidation process, a condensation process that obtains diacrylic anhydride from acrylic acid represented by Formula (1) and a condensation agent.

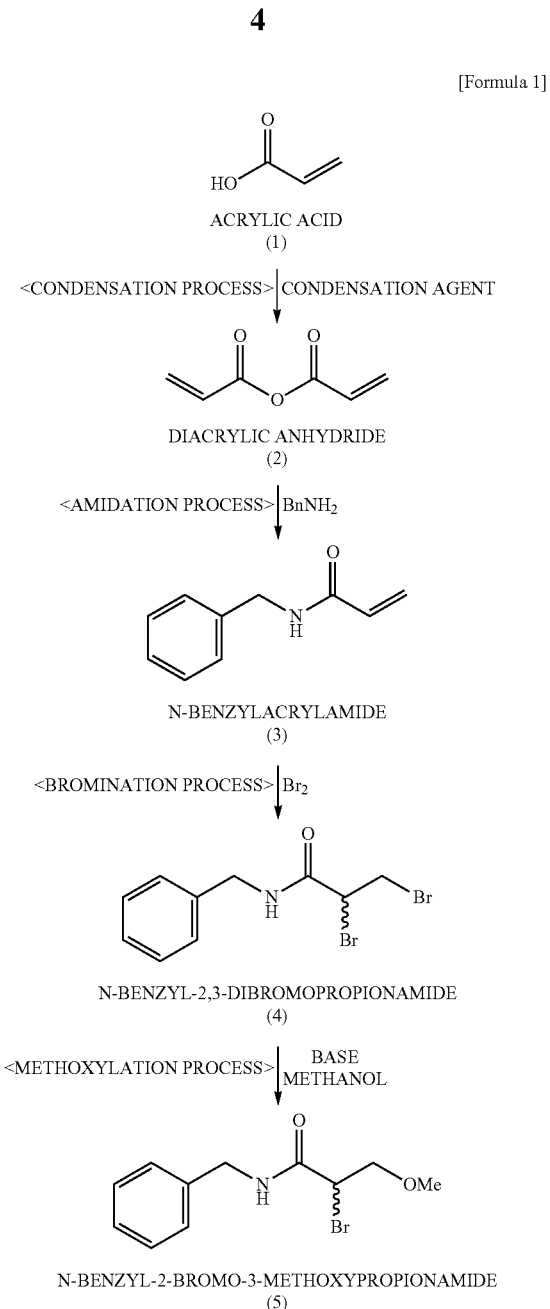

[Formula 1]

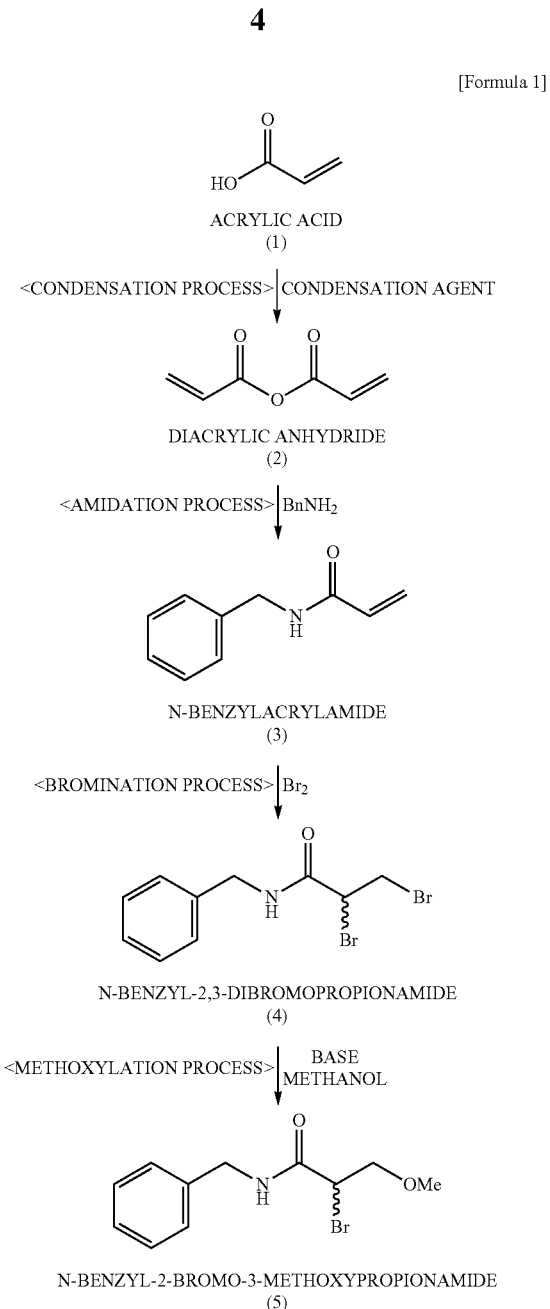

Condensation Process

Description will now be made in relation to the condensation process, which obtains diacrylic anhydride through an action of acrylic acid and a condensation agent in a solvent.

Material

The acrylic acid to be used in the condensation process may be one commercially available. The purity of the acrylic acid is not particularly restricted as far as the acrylic acid is industrially applicable, and is usually 90% or more, preferable 99% or more.

The condensation agent to be used in the condensation process condensates the acrylic acid into a dimer, and is preferable a dehydration condensation agent. Examples of the condensation agent are a carbodiimide-based condensation agent; an imidazole-based condensation agent; a triazine-based condensation agent; a phosphonium-based condensation agent; a halonium-based condensation agent; an uronium-based condensation agent; and a halouronium-based condensation agent. Examples of the carbodiimide-based condensation agent are 1-[3-(dimethylamino)propyl]-3-ethylcarbodiimide, N,N'-dicyclohexylcarbodiimide, and N,N'-diisopropylcarbodiimid, preferably N,N'-dicyclohexylcarbodiimide. Examples of the imidazole-based condensation agent are N,N'-carbonyldiimidazole, 1,1'-carbonyldi (1,2,4-triazole), N,N'-carbonyldiimidazole. An example of the triazine-based condensation agent is 4-(4,6-dimethoxy-1,3,5-triazine-2-yl) -4-methylmorpholinium=chloride. An example of the phosphonium-based condensation agent is trifluoromethanesulfonic acid(4,6-dimethoxy-1,3,5-triazine-2-yl)-(2-octoxy-2-oxoethyl) dimethylammonium. Examples of the halonium-based condensation agent are 1H-benzotriazole-1-yloxytris(dimethylamino)phosphoniumhexafluorophosphate, 1H-benzotriazole-1-yloxytripyrrolidinophosphoniumhexafluorophosphate, (7-azabenzotriazole-1-yloxy)tripyrrolidinophosphoniumhexafluorophosphate, chlorotripyrrolidinophoniumhexafluorophosphate, and bromotris(dimethylamino)phosphoniumhexafluorophosphate, 3-(diethoxyphosphoryloxy)-1,2,3-benzotriazine-4(3H)-one. Examples of an uronium-based condensation agent are O-(benzotriazole-1-yl)-N,N,N',N'-tetramethyluroniumhexafluorophosphate, O-(7-azabenzotriazole-1-yl)-N,N,N',N'-tetramethyluroniumhexa fluorophosphate, O-(N-succinimidyl)-N,N,N',N'-tetramethyluroniumtetrafluoroborate, O-(N-succinimidyl)-N,N,N',N'-tetramethyluroniumhexafluorophosphate, O-(3,4-dihydro-4-oxo-1,2,3-benzotriazine-3-yl)-N,N,N',N'-tetramethyluroniumtetrafluoroborate, S-(1-oxide-2-pyridyl)-N,N,N',N'-tetramethyluroniumtetrafluoroborate, O-[2-oxo-1(2H)-pyridyl]-N,N,N',N'-tetramethyluroniumtetrafluoroborate, and {{[(1-cyano-2-ethoxy-2-oxoethylidene)amino]oxy}-4-morpholino methylene}dimethylammoniumhexafluorophosphate. Examples of halouronium-based condensation agent are 2-chloro-1,3-dimethylimidazoliumhexafluorophosphate, 1-(chloro-1-pyrrolidinylmethylene) pyrrolidiniumhexafluorophosphate, 2-fluoro-1,3-dimethylimidazoliumhexafluorophosphate, and fluoro-N,N,N',N'-tetramethylformamidiniumhexafluorophosphate. Among these examples, the condensation material is preferably a carbodiimide-based condensation agent, an imidazole-based condensation agent, and a triazine-based condensation agent, more preferably a carbodiimide-based condensation agent. The condensation agent used in the condensation step may be a single kind or a combination of arbitrary two or more kinds at arbitrary ratio.

In relation to the ratio of the usage amount of the condensation agent to the acrylic acid, the usage amount of the condensation agent per acrylic acid of 1 mole is usually 0.3 moles or more, preferably 0.4 moles or more, more preferably 0.45 moles or more, and is usually 1 mole less, preferably 0.8 moles or less, more preferably 0.6 moles or less. When the usage amount of the condensation agent is excessively small, the reaction may fail to preferably proceed. Meanwhile, when the usage amount of the condensation agent is excessively large, a large amount of unreacted condensation agent remains and in cases where the reacting solution obtained after the condensation process is directly used in the amidation process, the remaining condensation agent hinders the reacting solution from being sufficiently mixed with benzylamine and therefore may affect the reaction.

The condensation process usually uses a solvent. The solvent used in the condensation process is not particularly limited as far as the solvent can dissolve or disperse the acrylic acid and the condensation agent to develop the reaction of the acrylic acid and the condensation agent, and can be a hydrophobic or hydrophilic organic solvent. Examples of the organic solvent are aromatic hydrocarbon such as toluene and xylene; aliphatic hydrocarbon such as n-hexane and n-heptane; ester such as ethyl acetate and isopropyl acetate; ether such as methyl-t-butyl ether, methylcyclopentylether, tetrahydrofuran, and 2-methyltetrahydrofuran; ketone such as acetone, methyl ethyl ketone, methyl isobutyl ketone; dimethylformamide; and dimethyl sulfoxide. Among these examples, aromatic hydrocarbon and aliphatic hydrocarbon being hydrophobic organic solvents are preferable, toluene, n-hexane, and n-heptane are more preferable from the viewpoints of cost and productivity, toluene is further preferable.

The lower limit of the usage amount of the solvent per acrylic acid of 1 gram is usually 1 mL or more, preferably 2 mL or more, more preferably 3 mL or more, and the upper limit thereof is usually 20 mL or less, preferably 15 mL or less, more preferably 10 mL or less.

Reaction Condition

The lower limit of the reaction temperature of the condensation process is usually −30° C. or more, preferably −10° C. or more, more preferably −5° C. or more, and the upper limit thereof is usually 30° C. or less, preferably 10° C. or less, and more preferably 5° C. or less.

Excessively low reaction temperature may sometimes fail to sufficiently develop the reaction while excessively high reaction temperature may dissolve the product.

The pressure when the reaction is conducted is normal pressure or pressurized pressure, and is usually satisfactorily normal pressure.

The reaction time is appropriately determined, is not particularly limited, and is usually 0.5 hours to 24 hours.

In the condensation process, the sequence to provide the acrylic acid and the condensation agent is not particularly limited as far as diacrylic anhydride is generated. For example, the reaction container is charged with one of the acrylic acid and the condensation agent along with the solvent, which are collectively regarded as the base solution, and the other is then charged under the reaction condition. Above all, it is preferable that a mixture of the condensation agent and the solvent are charged into the reaction container to be the base solution and then the acrylic acid is provided while the inner temperature is being controlled.

In providing the acrylic acid into the reaction system, a mixture of the acrylic acid and the solvent may be provided or the acrylic acid may be solely added. Otherwise, the acrylic acid may be provided in a manner of the combination of the above two manners. Likewise, in providing the condensation agent into the reaction system, a mixture of the condensation agent and the solvent may be provided or the condensation agent may be solely added. Otherwise, the condensation agent may be provided in a manner of the combination of the above two manners. The solvent to be mixed with the acrylic acid or the condensation agent may be the same as the solvent used in the condensation process.

In the condensation process, the reaction accompanies heat emission and therefore is preferably conducted while the inner temperature is being controlled. For this purpose, the condensation process preferably uses a reaction container with a stirring container and temperature adjustable equipment such as a jacket that is able to heat and cool an object.

The condensation process is preferable carried out in an inert-gas atmosphere. The inert gas is not particularly limited and is exemplified by nitrogen, argon, and helium, among which nitrogen is preferable.

As described above, the condensation process, which causes the acrylic acid to react with the condensation agent, can obtain the reaction solution containing a diacrylic anhydride. The deacrylic anhydride obtained in the condensation process can be used in the amidation process. Alternatively, after the reaction of the condensation process, the reacting solution containing the diacrylic anhydride can be used in the amidation process. In this case, since the reacting solution may contain by-products being originated from the condensation agent and being generated during the reaction, the by-products may be appropriately removed through separation or solid-liquid separation. For example, in cases where N,N'-dicyclohexylcarbodiimide is used as the condensation agent, dicyclohexylurea is deposited as a by-product and is preferably removed by solid-liquid separation. In this case, the temperature for solid-liquid separation is preferably 5° C. or less for separation of the deposited by-product. Furthermore, the separated by-product may be rinsed to recover the diacrylic anhydride adhering to the by-product. A solvent used for rinsing is not particularly limited and may be the same as the solvent used in the above condensation process. The diacrylic anhydride contained in the reacting solution after the solid-liquid separation of the by-product can be isolated and purified by known means such as extraction, concentration, evaporation, and chromatography.

Amidation Process

Next, description will now be made in relation to the amidation process, which causes the diacrylic anhydride to react with benzylamine in a solvent and thereby obtains NBA.

Material

As the diacrylic anhydride to be used in the amidation process, the reacting solution obtained in the condensation process may be directly used, the reacting solution obtained in the condensation process and then subjected to the solid-liquid separation may be used, the diacrylic anhydride separated from the reacting solution obtained in the condensation process may be used, or diacrylic anhydride commercially available may be used. Above all, the reacting solution obtained in the condensation process is preferably used, and the reacting solution obtained in the condensation process and then subjected to the solid-liquid separation is more preferably used.

The lower limit of the usage amount of benzylamine per diacrylic anhydride of 1 mole is usually 0.2 moles or more, preferably 0.5 moles or more, more preferably 0.7 moles or more, further preferably 0.9 moles or more, and the upper limit thereof is usually 3 moles or less, preferable 1.5 moles or less, more preferably 1.3 moles or less, further preferably 1.1 moles or less.

If the usage amount of benzylamine is excessively small, the yield may be degraded. In the meantime, if the usage amount is excessively large, a by-product may be generated.

The amidation process usually uses a solvent. The solvent used in the amidation process is not particularly limited as far as the solvent can dissolve or disperse diacrylic anhydride and benzylamine to develop the reaction of diacrylic anhydride and benzylamine, and can be usually an organic solvent. The organic solvent may be of hydrophobic or hydrophilic, and preferably contains a hydrophobic organic solvent.

Examples of a hydrophobic organic solvent are aromatic hydrocarbon such as toluene and xylene; aliphatic hydrocarbon such as n-hexane and n-heptane; and ester such as ethyl acetate and isopropyl acetate. Among these examples, toluene, n-hexane, and n-heptane are preferable from the viewpoints of cost and productivity, and toluene is more preferable.

Examples of the hydrophilic organic solvent are alcohol such as methanol, ethanol, isopropyl alcohol, and butanol; ether such as dimethyl ether, diethyl ether, diisopropyl ether, tetrahydrofuran, 2-methyltetrahydrofuran, tetrahydropyran, and 1,4-dioxane; ketone such as acetone and methyl ethyl ketone; dimethylformamide; and dimethyl sulfoxide. Among these examples, ether is preferable, and tetrahydrofuran, 2-methyltetrahydrofuran, tetrahydropyran, and 1,4-dioxane are more preferable.

In the present invention, the solvent of the amidation process may be a combination of water and an organic solvent. In other words, the amidation process preferably uses a mixture solvent of the above organic solvent and water, in particular, the hydrophobic organic solvent and water. In this case, the amidation process is carried out in a two-phase system including an organic-solvent phase and the aqueous phase. The amidation process performed in the two-phase system can suppress the usage amount of benzylamine and can reduce the production cost. Furthermore, reactivity of benzylamine can be enhanced by removing the acrylic acid, which is a by-product of the amidation process, from the organic-solvent phase to the aqueous phase, so that the yield of NBA can be increased.

In cases where the amidation process is carried out in a two-phase system, the lower limit of the usage ratio of water to the organic solvent is usually 0.1 times by weight or more, preferably 0.2 times by weight or more, further preferably 0.3 times by weight or more, and the upper limit thereof is usually 1 time by weight or less, preferably 0.9 times by weight or less, further preferably 0.8 times by weight or less.

The lower limit of the usage amount of the solvent per diacrylic anhydride of 1 gram is usually 1 mL or more, preferably 2 mL or more, further preferably 3 mL or more, and the upper limit thereof is usually 25 mL or less, preferably 20 mL or less, further preferably 15 mL or less.

From the viewpoint of enhancing the reactivity, the amidation process is preferably carried out in the presence of base. In other words, a base is preferably contained in the solvent. In particular, it is preferable that the solvent is a mixture solvent of an organic solvent and water and contains a base. Further preferably, the solvent is a mixture solvent of a hydrophobic organic solvent and water, and a base is contained in the aqueous phase. For example, this can be achieved by that the solvent is a mixture solvent of an organic solvent containing a hydrophobic organic solvent and an aqueous solution containing a base and the reaction is conducted in a two-phase system containing an organic-solvent phase and an aqueous phase. In this case, the reactivity of benzylamine is enhanced by removing acrylic acid, which is a by-product generated in the amidation process, from the organic-solvent phase to the aqueous phase and neutralizing acrylic acid contained in the aqueous phase with the base, so that the yield of NBA can be further increased.

The base can be at least one kind selected from a group consisting of inorganic bases and organic bases, and is usually an inorganic base. The inorganic base is not particularly limited and is an inorganic base compound exemplified by alkali metal hydroxide such as sodium hydroxide and potassium hydroxide; alkali metal carbonate such as sodium carbonate and potassium carbonate; alkali metal hydrogencarbonate such as sodium hydrogencarbonate and potassium hydrogencarbonate; alkali metal acetate such as sodium acetate and potassium acetate. An organic base is not particularly limited and is an organic base compound exemplified by heterocyclic amine such as pyrrolidine, pyrrole, piperidine, and pyridine; organic amine such as dimethylamine, trimethylamine, diethylamine, and triethylamine. Among these examples, the base is preferably an inorganic base such as sodium hydroxide, sodium carbonate, potassium hydroxide, potassium carbonate, and sodium hydrogencarbonate, more preferably sodium hydroxide, potassium carbonate, and sodium hydrogencarbonate. The base to be used in the amidation process may be a single kind or a combination of arbitrary two or more kinds at an arbitrary ratio.

The above base exists in the solvent and neutralizes generated acrylic acid. Since excessively high strength of the base may decompose the material diacrylic anhydride, it is preferable that a weak base is usually used. However, in cases where the reaction is conducted in a two-phase system by using a mixture solvent containing a hydrophobic organic solvent and water as the solvent, using a strong base brings a preferable result.

The lower limit of the pH of the aqueous phase in the reaction mixture is usually 7.2 or more, and in particular, when a weak base is used, is usually 7.2 or more, preferably 7.5 or more, further preferably 8 or more. The upper limit of the pH thereof is usually 11 or less, preferably 10.5 or less, more preferably 10 or less. When a strong base is used, the upper limit of the pH thereof is usually 11 or more, preferably 11.5 or more, further preferably 12 or more. In cases where a hydrophobic organic solvent is solely used as the solvent, it is satisfactory that the aqueous phase separated from a mixture of the hydrophobic organic solvent with water of 10 times by weight has a pH of the above range.

The usage amount of the base per diacrylic anhydride of 1 mole, however varying to some extent with the kind of base to be used, has a lower limit of usually 0.5 moles or more, preferably 0.7 moles or more, further preferably 0.9 moles or more, and has an upper limit of usually 3 moles or less, preferably 2 moles or less, further preferably 1.2 moles or less. A usage amount within the above range can suppress generation of decomposed product.

Reaction Condition

The reaction temperature of the amidation process, being not particularly limited as far as the reaction proceeds, has a lower limit of usually 0° C. or more, preferably 10° C. or more, more preferably 20° C. or more, and has an upper limit of usually 50° C. or less, preferably 40° C. or less, and more preferably 30° C. or less.

Excessively low reaction temperature may sometimes fail to sufficiently develop the reaction while excessively high reaction temperature may dissolve the product. It is preferable that the temperature of the reaction mixture during the reaction is kept to be constant.

The pressure when the reaction is conducted is normal pressure or pressurized pressure, and is usually satisfactorily normal pressure.

The reaction time is appropriately determined, is not particularly limited, and is usually 0.5 hours to 24 hours.

In the amidation process, the sequence to provide diacrylic anhydride and benzylamine is not particularly limited. For example, the reaction container is charged with one of diacrylic anhydride and benzylamine along with the solvent, which are collectively regarded as the base solution, and the other is then charged under the reaction condition. Above all, it is preferable that a mixture of the benzylamine and the solvent, and an aqueous solution containing a base are charged into the reaction container and stirred to be the base solution, and then diacrylic anhydride is provided to the mixture. This can suppress the decomposition of diacrylic anhydride and also increase the yield of NBA. Here, it is further preferable that diacrylic anhydride is provided while the inner temperature of the base solution is being controlled.

In providing diacrylic anhydride into the reaction system, a mixture of diacrylic anhydride and a solvent may be provided or a diacrylic anhydride may be solely added. Otherwise, diacrylic anhydride may be provided in a manner of the combination of the above two manners. Likewise, in providing benzylamine into the reaction system, a mixture of benzylamine and a solvent may be provided or benzylamine may be solely added. Otherwise, benzylamine may be provided in a manner of the combination of the above two manners. The solvent to be mixed with diacrylic anhydride or the benzylamine may be the same as the solvent used in the amidation process, preferably a hydrophobic organic solvent.

In the amidation process, the base is provided in the form of a mixture with the solvent, in a single form of the base, or in combination of the former two manners. Above all, it is preferable that the base is provided in the form of an aqueous solution in which the base and the water are mixed. In providing an aqueous solution in which the base and the water are mixed, the aqueous solution to be used may be adjusted to have the concentration of the base of 5 wt % to 20 wt %, for example. In cases where the solvent is a mixture solvent of an organic solvent and water, the base can exist in the water. In this case, the reaction is preferably conducted under the stirred condition.

The amidation process is preferably carried out in an inert-gas atmosphere. The inert gas is not particularly limited and is exemplified by nitrogen, argon, and helium, among which nitrogen is preferable.

NBA obtained in the amidation process can be used in the bromination process. After the reaction of the amidation process, the reacting solution containing NBA can be directly used in the bromination process. Alternatively, NBA may be isolated from the reacting solution and then used in the bromination process. From the aspect of the industrial productivity, it is preferable that the reacting solution obtained in the amidation process is directly used in the bromination process.

In case where the reaction of the amidation process is conducted in the single phase system only of an organic-solvent phase in the absence of a base, the reacting solution can be directly used in the bromination process. In cases where the reaction of the amidation process is conducted in the single phase system only of an organic-solvent phase in the presence of a base, the remaining base is neutralized by, for example, washing with an acid solution such as hydrochloric acid after the completion of the reaction, the aqueous phase is removed by separation, and finally the organic-solvent phase can be used in the bromination process. In cases where the reaction is conducted in the two-phase system including an organic-solvent phase and the aqueous phase, the aqueous phase is removed by separation after the completion of the reaction and the organic-solvent phase can be used in the bromination process. NBA contained in the organic-solvent phase can be isolated and purified by various publically known manners such as extraction, concentration, evaporation, deposition, and column chromatography. For example, NBA can be obtained by removing the organic solvent through vacuum concentration on the reacting solution after the completion of the reaction and subsequent vacuum drying.

Bromination Process

Next, description will now be made in relation to the bromination process, which causes NBA to react with bromine in the solvent to thereby obtain BBA.

Material

As NBA used in the bromination process, the reacting solution obtained in the amidation process maybe directly used, NBA isolated from the reacting solution obtained in the amidation process may be used, or commercially available NBA can be used. Above all, it is preferable from an aspect of industrial productivity that the reacting solution obtained in the amidation process is directly used. In cases where the amidation process has been carried out in a two-phase system including an organic-solvent phase and a aqueous phase, the organic solvent phase obtained by removing the aqueous phase is preferably used.

The lower limit of the usage amount of bromine per NBA of 1 mole is usually 0.3 moles or more, preferably 0.5 moles or more, more preferably 0.7 moles or more, and the upper limit thereof is usually 3 moles or less, preferable 2 moles or less, more preferably 1.5 moles or less.

The bromination process usually uses a solvent. The solvent used in the bromination process is not particularly limited as far as the solvent can dissolve or disperse NBA and bromine to develop the reaction of NBA and bromine, and can be usually the same as the solvent used in the condensation process. Besides, the mixture of an organic solvent and water can be used for the reaction.

The lower limit of the usage amount of the solvent per NBA of 1 gram is usually 1 mL or more, preferably 3 mL or more, further preferably 5 mL or more, and the upper limit thereof is usually 25 mL or less, preferably 20 mL or less, more preferably 15 mL or less.

The bromination process is preferably carried out under an acid condition, so that decomposition of NBA can be suppressed. The lower limit of pH of the reaction system during the bromine reaction is usually pH 2 or more, preferably pH 3 or more, and the upper limit of thereof is usually less than pH 7, preferably pH 6 or less. The manner of adjusting the pH is not particularly limited and is exemplified by mixing with acid such as acetic acid, hydrochloric acid, and sulfuric acid.

Reaction Condition

The reaction temperature of the bromination process has a lower limit of usually 0° C. or more, preferably 10° C. or more, more preferably 20° C. or more, and has an upper limit of usually 50° C. or less, preferably 40° C. or less, and more preferably 30° C. or less.

The pressure when the reaction is conducted is normal pressure or pressurized pressure, and is usually satisfactorily normal pressure.

The reaction time is appropriately determined, is not particularly limited, and is usually 0.5 hours to 24 hours.

The reaction of the bromination process is preferably carried out by providing bromine to a base solution corresponding to a mixture solution containing NBA and the solvent. In providing bromine to the reaction system, a mixture of bromine and the solvent may be provided, bromine may be solely provided, and bromine may be provided in combination of the above two manners.

In providing the acid in the bromination process, an aqueous solution in which acid and water are mixed or solely acid may be provided. Otherwise, the acid may be provided in a combination of the above two manners. Above all, the acid is usually provided in the form of an aqueous solution, which allows the bromination process to proceed in a two-phase system containing an organic-solvent phase and the aqueous phase. In this case, the reaction is preferably conducted under a stirred condition.

After the reaction, a dehalogenation process is preferably carried out using a dehalogenation agent to inactivate unreacted bromine.

The dehalogenation agent is not particularly limited and is exemplified by a sulfite such as sodium sulfite, sodium hydrogensulfite, potassium sulfite, ammonium sulfite, and ferrous sulfite; and thiosulfate such as sodium thiosulfate, potassium thiosulfate, calcium thiosulfate, and ammonium thiosulfate. Among these example, sulfite is preferable among which sodium sulfite is preferable.

The lower limit of the dehalogenation agent per bromine being used of 1 mole is usually 0.1 moles or more, preferably 0.3 moles or more, and the upper limit thereof is usually 1 mole or less, preferably 0.7 moles or less.

If an excessively large amount of the dehalogenation agent is used, the solvent comes to exhibit strong basic and may increase by-product.

The dehalogenation agent is provided to the reaction system solely or in the form of a mixture with water previously prepared. Usually, the dehalogenation agent is provided in the form of an aqueous solution. The dehalogenation agent is usually provided after the reaction of bromine with the NBA is completed.

The dehalogenation process is preferably carried out under an acid condition, so that decomposition of BBA can be suppressed. The lower limit of pH of the reaction system while the dehalogenation process is usually pH 2 or more, preferably pH3 or more, and the upper limit of thereof is usually less than pH 7, preferably pH 6 or less. The manner of adjusting the pH is not particularly limited and is exemplified by mixing with acid such as acetic acid, hydrochloric acid, and sulfuric acid. The sequence of providing the acid and the dehalogenation agent is not particularly limited. The dehalogenation agent may be provided after the acid is provided, and the acid may be provided after the halogenation agent is provided. The dehalogenation agent is preferably provided after the acid is provided.

In cases where the reaction is conducted in a two-phase system including an organic-solvent phase and an aqueous phase, the aqueous phase is removed by separation after the completion of the reaction. BBA contained in the organic-solvent phase can be isolated and purified by various publically known manners such as extraction, concentration, evaporation, deposition, and column chromatography. For example, BBA can be obtained by depositing the crystal by cooling the reaction system after completion of the reaction, solid-liquid separating the deposited crystal, washing the crystal with toluene, vacuum drying the crystal.

Methoxylation Process

In succession, description will now be made in relation to the methoxylation process, which causes BAA to react with methanol in the presence of a base and thereby obtains BMBA.

Material

As BBA used in the methoxylation process, BBA obtained in the bromination process can be used.

The base used in the methoxylation process is not particularly limited and is exemplified by an inorganic base compound exemplified by alkali metal hydroxide such as lithium hydroxide, sodium hydroxide, and potassium hydroxide, alkali metal carbonate such as sodium carbonate and potassium carbonate, alkali metal hydrogencarbonate such as sodium hydrogencarbonate and potassium hydrogencarbonate, and alkali metal acetate such as sodium acetate, and potassium acetate; and alkali metal methoxide exemplified by lithium methoxide, sodium methoxide, and potassium methoxide. Among these examples, the base is preferably sodium hydroxide, sodium carbonate, potassium hydroxide, and potassium carbonate, more preferably sodium hydroxide.

The lower limit of the base per BBA of 1 mole is usually 1 mole or more, preferably 2 moles or more, and the upper limit thereof is usually 10 moles or less, preferably 5 moles or less.

In cases where an inorganic base compound is used as the base, the reaction of the methoxylation process is conducted in methanol. In cases where alkali metal methoxide is used as the base, the reaction is usually conducted in methanol, but may be conducted in another type of solvent as far as the reaction of the methoxylation proceeds. Examples of the solvent is alcohol such as ethanol, propanol, isopropyl alcohol, and tert-butyl alcohol; ether such as tetrahydrofuran; aromatic hydrocarbon such as toluene, xylene, and ethylbenzene; aromatic-halogen-containing hydrocarbon such as chlorobenzene and dichlorobenzene; and aliphatic hydrocarbon such as n-hexane and n-heptane.

The lower limit of the usage amount of methanol per 1 gram of BBA is usually 1 mL or more, preferably 1.5 mL or more, more preferably 2 mL or more, and the upper limit thereof is usually 20 mL or less, preferably 15 mL or less, more preferably 10 mL or less.

Reaction Condition

The lower limit of the reaction temperature of the methoxylation process is usually −20° C. or more, preferably −10° C. or more, more preferably 0° C. or more, and the upper limit thereof is usually 80° C. or less, preferably 70° C. or less, and more preferably 50° C. or less.

The pressure when the reaction is conducted is normal pressure or pressurized pressure, and is usually satisfactorily normal pressure.

The reaction time is appropriately determined, is not particularly limited, and is usually 0.1 hours to 100 hours, preferably 0.2 hours to 80 hours, more preferably 0.3 to 24 hours.

The sequence of providing BAA, the base, and methanol is not particularly limited as far as BMBA is produced. For example, the reaction container is charged with one of BBA and the base along with methanol, which are collectively regarded as the base solution, and the other is then charged under the reaction condition. Above all, it is preferable that a mixture of the BBA and methanol is charged into the reaction container to be a base solution and then base is provided while the inner temperature is being controlled.

In providing BBA to the reaction system, BBA may be provided in a form of a mixture with methanol or BBA may be solely provided. Otherwise, BBA may be provided in the combination of two above manners. Likewise, in providing the base to the reaction system, the base may be provided in a form of a mixture with methanol or the base may be solely provided. Otherwise, the base may be provided in the combination of two above manners.

BBA may be provided all at once or dividedly several times. The base maybe provided all at once or dividedly several times.

The methoxylation process is preferably carried out in an inert-gas atmosphere. The inert gas is not particularly limited and is exemplified by nitrogen, argon, and helium, among which nitrogen is preferable.

After the completion of the reaction, BMBA contained in the reacting solution can be isolated and purified by various publically known manners such as extraction, concentration, evaporation, deposition, and column chromatography. For example, BMBA can be obtained by depositing the crystal by cooling the reaction system through vacuum evaporation of methanol or through supplying water after completion of the reaction, solid-liquid separating the deposited crystal, washing the crystal with water, vacuum drying the crystal.

As described above, the method for producing BMBA of the present invention includes the amidation process, the bromination process, and the methoxylation process, and can obtain BMBA that is to be used as an intermediate for synthesizing lacosamide. Including the amidation process that obtains NBA through the reaction of diacrylic anhydride with benzylamine, the method of producing of the present invention can obtain BBA and BMBA at higher yields than a method for synthesizing NBA by using acrylonitrile and benzyl alcohol (for example, Patent Literature 2). In addition, the method for producing of the present invention can use acrylic acid, which is widely put into market, as the starting material and does not require a large amount of concentrated sulfuric acid, which can eliminate the requirement for a treatment of a large amount of waste solution of over acidity. Advantageously, the present invention provides an industrially-preferable method that is excellent in productivity and less in impact to the environment.

2. Method for Producing N-benzyl-2,3-dibromopropionamide

The method for producing BAA of the present invention includes at least the amidation process and the bromination process described above. Further, the method for producing BBA of the present invention may include the above condensation process before the amidation process.

Likewise the above method for producing BMBA, the method for producing of the present invention can safely produce BBA at a high yield and at a low cost. Here, BBA can be used as an intermediate for synthesizing BMBA and lacosamide. For example, BMBA can be obtained by carrying out the successive methoxylation process using BBA obtained by the present method for producing.

3. Method for Producing N-benzylacrylamide

The method for producing NBA of the present invention includes at least the above amidation process. Further, the method for producing NBA of the present invention may include the above condensation process before the amidation process.

Obtaining NBA by the reaction of diacrylic anhydride with benzylamine, the present method for producing can safely produce NBA at a high yield, suppressing polymerization and the resultant polymerization heat accompanied by the polymerization which are generated in cases where acrylonitrile is used as starting material (for example, Patent Literature 2). Here, NBA can be used as an intermediate for synthesizing BBA, BMBA, and lacosamide. For example, BMBA can be obtained by carrying out the successive bromination process and methoxylation process, using NBA obtained by the present method for producing.

EXAMPLES

[Example 1 (method for producing BBA)]
<Step 1: synthesizing diacrylic anhydride>

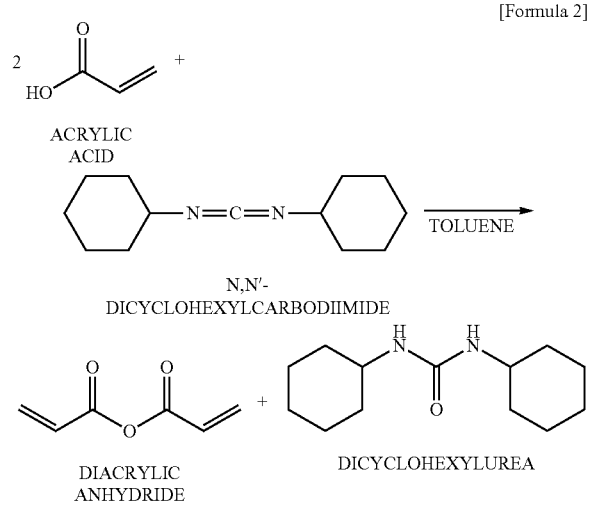

[Formula 2]

N,N'-dicyclohexylcarbodiimide (hereinafter, sometimes referred to as "DCC") (20.5 g, 0.10 moles) serving as the condensation agent and toluene (64.8 g, 75 mL) serving as the solvent were charged in a 100-mL reaction container equipped with a nitrogen gas supplying pipe, a thermometer, and a stirrer in a nitrogen atmosphere, and the reacting solution was cooled such that the inner temperature was in a temperature range of -5 °C. to 5 °C., being stirred at 500 rpm. After the cooling, acrylic acid (15.1 g, 0.21 moles) serving as the material was dropped into the toluene solution of DCC, being stirred, while the inner temperature was being controlled in the above range. After the completion of the dropping, the reaction solution was further stirred for 30 minutes under a condition of the inner temperature of 0 °C. to proceed the reaction.

After the completion of the stirring, the white solid of deposited dicyclohexylurea was filtered through suction filtration and the dicyclohexylurea was washed with toluene (25.9 g, 30 mL) to obtain the washing solution. Then, the filtrate and the washing solution were mixed and thereby a toluene solution of diacrylic anhydride was obtained.

Step 2: Synthesizing NBA

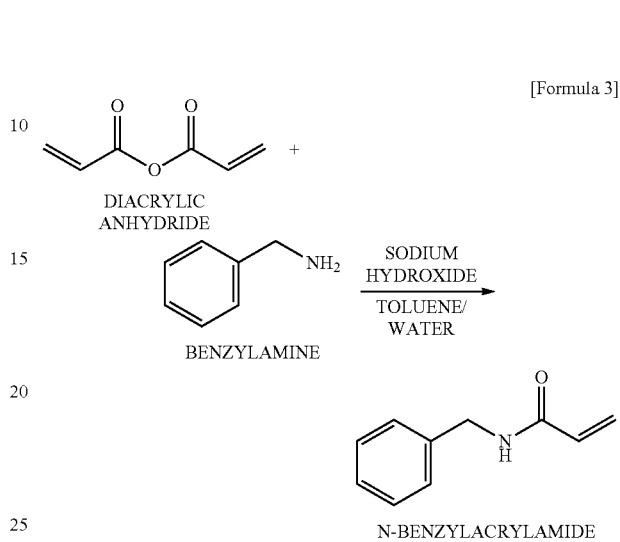

[Formula 3]

Benzylamine (11.7 g, 0.11 moles) serving as the material, toluene (25.9 g, 30 mL) serving as the solvent and 9% sodium hydroxide aqueous solution (87.9 g, 0.20 moles) serving as the base were charged in a 500-mL reaction container equipped with a nitrogen gas supplying pipe, a thermometer, and a stirrer in a nitrogen atmosphere, and the reacting solution was cooled such that the inner temperature came to be 0° C., being stirred at 300 rpm. After the cooling, the reacting solution was regarded as a base solution and the toluene solution of diacrylic anhydride obtained in Step 1 was dropped into the base solution, being stirred, such that the inner temperature did not exceed 5° C., i.e., being controlled in the temperature range of 0° C. to 5° C. After the completion of the dropping, the jacket temperature was raised to 25° C. and the reaction solution was stirred for 30 minutes.

After the completion of the stirring, the reaction solution was stood still for 5 minutes and the aqueous phase was removed by separation to obtain a toluene solution of NBA.

Step 3: Synthesizing BBA

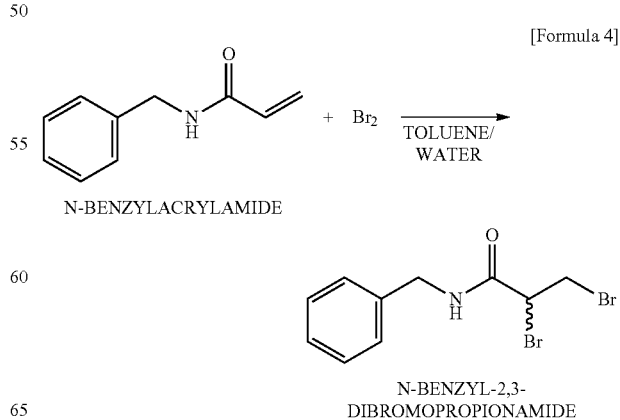

[Formula 4]

Water (7.5 g) was supplied to the toluene solution of NBA and being obtained in Step 2, and 2 mol/L hydrochloric acid serving as the acid was added so that the pH of the aqueous phase was adjusted to 3. After the adjusting the pH, bromine (17.9 g, 0.11 moles) was dropped into the reaction solution, while being stirred at 300 rpm, over 30 minutes. After the completion of the dropping, the reaction solution was further stirred for 2 hours under a condition of the inner temperature of 25° C. to proceed the reaction.

After the completion of the stirring, 15% sodium sulfite solution (95.5 g, 0.11 moles) serving as the dehalogenation agent was provided to the reacting solution, and 2 mol/L hydrochloric acid serving as the acid was added so that the pH of the aqueous phase was adjusted to 4. After the adjusting the pH, the inner temperature of the reacting solution is raised to 65° C., the reacting solution was stood still for 2 minutes and then the aqueous phase was removed by separation.

After removing the aqueous phase, the jacket temperature of the reaction container was cooled to 52° C., while the toluene solution of BBA was being stirred at 300 rpm, and deposition of crystal was confirmed. After the deposition of crystal, the inner temperature was further cooled to 0° C., and the slurry containing BBA was stirred at 0° C. for 2 hours. After the stirring, the deposited solid is filtered by suction filtration, the filtered solid was washed with toluene of 13.0 g, and wet crystal of BBA was obtained. The obtained wet crystal was vacuum dried at the outer temperature of 45° C. and thereby BBA (23.4 g, at a yield of 67% to benzylamine) in the form of white solid was obtained. For the following results of NMR measurement on BBA and measurement of the melting point, the generated product was ascertained to be BBA. In Examples of the present description, NMR measurement was conducted with AV400N manufactured by Bruker Corporation.

$^1$H-NMR (400 MHz, CDCl$_3$)

δ: 3.86 (1H, dd, J=4.4 Hz, 5.8 Hz), 4.01 (1H, dd, J=2.0 Hz, 8.3 Hz), 4.48-4.53 (3H, m), 6.40 (1H, br), 7.30-7.36 (5H, m)

melting point: 120° C.

Example 2

Method for Producing BMBA

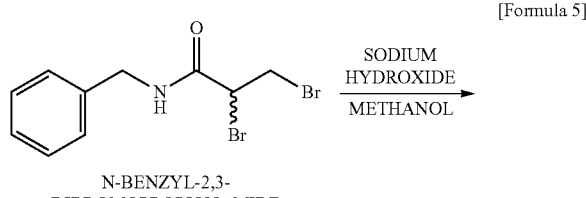

[Formula 5]

N-BENZYL-2,3-DIBROMOPROPIONAMIDE

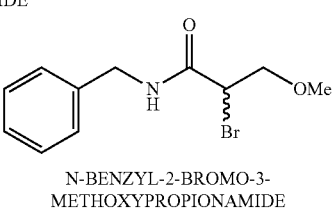

N-BENZYL-2-BROMO-3-METHOXYPROPIONAMIDE

BBA (22.0 g, 0.069 moles) obtained in Example 1 and methanol (66.1 g, 83 mL) were charged in a 100-mL reaction container equipped with a nitrogen gas supplying pipe, a thermometer, and a stirrer in a nitrogen atmosphere, and the reacting solution was cooled such that the inner temperature came to be 20° C., being stirred at 400 rpm. After the cooling, powder-form sodium hydroxide (5.50 g, 0.138 moles) serving as a base was charged dividedly over 6 times such that the inner temperature did not exceed 30° C. After the charging, the reaction was developed, keeping the inner temperature 20° C. and keeping the reaction system being stirred for 30 minutes. After the stirring, water (66.0 g) was dropped and deposition of crystal was conformed. After the deposition of crystal, the outer temperature was cooled to −2° C. After the cooling, the reaction system was further stirred at the inner temperature of 0° C. for 1.5 hours.

After the stirring, the deposited solid was suction filtered, and the obtained crystal was washed with water (22.0 g). After the washing, the obtained solid was vacuum dried at 45° C., and thereby BMBA (18.0 g, at a yield of 96% to BBA, chemical purity of 97.6 area %) in the form of white solid was obtained. The chemical purity (area %) was measured by means of HPLC on the following condition with Agilent 1290 manufactured by Agilent Technologies, Inc.

column: Cadenza CD-C18 (150 mm×4.6 mm, 3 μm)
mobile phase A: 0.1% TFA aqueous solution
mobile phase B: acetonitrile
gradient B solution concentration: (15%/0 min.)→(50%/15 min.)→(50%/20 min)
flow rate: 1 mL/min.
injection volume: 5 μL
detecting wavelength: 215 nm
column temperature: 40° C.
analysis time: 20 min.

For the following results of NMR measurement on BMBA and measurement of the melting point, the generated product was ascertained to be BMBA.

$^1$H-NMR (400 MHz, CDCl$_3$)

δ; 3.43 (3H, s), 3.90 (2H, ddd, J=14.4 Hz, 5.9 Hz, 4.8 Hz), 4.44 (1H, t, J=4.8 Hz), 4.48 (2H, d, J=5.6 Hz), 6.87 (1H, br), 7.26-7.32 (5H, m)

melting point: 79° C.

Example 3 (Method for Producing NBA)

A toluene solution of NBA was prepared in the manner same as Steps 1 and 2 of Example 1 except for that the usage amounts of DCC, toluene, and acrylic acid in Step 1 were changed to 7.16 g (0.035 moles), 41.5 g, and 5.04 g (0.070 moles), respectively, and the usage amount of benzylamine and 9% sodium hydroxide aqueous solution in Step 2 were changed to 3.75 g (0.035 moles) and sodium hydrogencarbonate 3.00 g (0.036 moles).

Toluene is evaporated from the obtained toluene solution of NBA through vacuum concentration. After the concentration, the reaction system was vacuum dried at 45° C. and thereby NBA of 5.65 g (chemical purity of 97 area %) in the form of white solid was obtained. A chemical purity (area %) was measured by means of HPLC on the following condition with Agilent 1290 manufactured by Agilent Technologies, Inc.

column: Cadenza CD-C18 (150 mm×4.6 mm, 3 μm)
mobile phase A: 0.1% TFA aqueous solution
mobile phase B: acetonitrile
gradient B solution concentration: (15%/0 min.)→(50%/15 min.)→(50%/20 min)
flow rate: 1 mL/min.
injection volume: 5 μL detecting wavelength: 215 nm
column temperature: 40° C.
analysis time: 20 min.

For the following results of NMR measurement on NBA and measurement of the melting point, the generated product was ascertained to be NBA.

$^1$H-NMR (400 MHz, CDCl$_3$) 67.25-7.33 (m, 5H), 6.29 (dd, 1H, J=1.5, 15.4 Hz), 6.25 (1H, br), 6.13 (dd, 1H, J=6.8, 10.2 Hz), 5.64 (dd, 1H, J=1.6, 8.7 Hz), 4.48 (d, 2H, J=5.8 Hz)

melting point: 65° C.

The invention claimed is:

1. A method for producing N-benzyl-2-bromo-3-methoxypropionamide comprising:
   in sequence,
   an amidation process that causes diacrylic anhydride to react with benzylamine in a two-phase system including an organic-solvent phase and an aqueous phase comprising an inorganic or organic base to obtain N-benzylacrylamide;
   a bromination process that causes N-benzylacrylamide to react with bromine in a solvent to obtain N-benzyl-2,3-dibromopropionamide; and
   a methoxylation process that causes N-benzyl-2,3-dibromopropionamide to react with methanol in the presence of a base to obtain N-benzyl-2-bromo-3-methoxypropionamide.

2. The method according to claim 1, wherein diacrylic anhydride used in the amidation process is obtained by causing acrylic acid to react with a condensation agent in a solvent.

3. A method for producing N-benzyl-2,3-dibromopropionamide comprising:
   in sequence,
   an amidation process that causes diacrylic anhydride to react with benzylamine in a two-phase system including an organic-solvent phase and an aqueous phase comprising an inorganic or organic base to obtain N-benzylacrylamide; and
   a bromination process that causes N-benzylacrylamide to react with bromine in a solvent to obtain N-benzyl-2,3-dibromopropionamide.

4. The method according to claim 3, wherein the condensation agent is a carbodiimide-based condensation agent.

5. A method for producing N-benzylacrylamide comprising an amidation process that causes diacrylic anhydride to react with benzylamine in a two-phase system including an organic-solvent phase and an aqueous phase comprising an inorganic or organic base to obtain N-benzylacrylamide.

6. The method according to claim 5, wherein diacrylic anhydride used in the amidation process is obtained by causing acrylic acid to react with a condensation agent in a solvent.

7. The method according to claim 6, wherein the condensation agent is a carbodiimide-based condensation agent.

8. The method of claim 1 wherein the aqueous phase comprises an inorganic base.

9. The method of claim 3 wherein the aqueous phase comprises an inorganic base.

10. The method of claim 5 wherein the aqueous phase comprises an inorganic base.

* * * * *